(12) United States Patent
Hamada et al.

(10) Patent No.: US 10,466,168 B2
(45) Date of Patent: Nov. 5, 2019

(54) RESIN DETERMINATION METHOD AND RESIN DETERMINATION APPARATUS

(71) Applicant: Panasonic Intellectual Property Management Co., Ltd., Osaka (JP)

(72) Inventors: Shingo Hamada, Osaka (JP); Noriyuki Suzuki, Osaka (JP); Naoya Miyaji, Osaka (JP); Naoshi Yamaguchi, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/158,048

(22) Filed: Oct. 11, 2018

(65) Prior Publication Data
US 2019/0128801 A1    May 2, 2019

(30) Foreign Application Priority Data

Oct. 30, 2017   (JP) ................. 2017-209070

(51) Int. Cl.
*G01J 5/02*         (2006.01)
*G01N 21/3563*    (2014.01)
*G01N 21/3559*    (2014.01)
*G02B 5/02*         (2006.01)

(52) U.S. Cl.
CPC ..... *G01N 21/3563* (2013.01); *G01N 21/3559* (2013.01); *G02B 5/021* (2013.01); *G02B 5/0221* (2013.01)

(58) Field of Classification Search
CPC .. G02B 5/021; G02B 5/0221; G01N 21/3563; G01N 21/3559
See application file for complete search history.

(56) References Cited

U.S. PATENT DOCUMENTS

| | | |
|---|---|---|
| 8,975,586 B2 | 3/2015 | Krolak et al. |
| 9,024,224 B2 | 5/2015 | Mase et al. |
| 9,341,566 B2 | 5/2016 | Kinugawa et al. |
| 2010/0053785 A1* | 3/2010 | Nishi ............... F21S 11/00 359/838 |

(Continued)

FOREIGN PATENT DOCUMENTS

| | | |
|---|---|---|
| JP | 2012-145528 | 8/2012 |
| JP | 2013-064726 | 4/2013 |

(Continued)

OTHER PUBLICATIONS

Extended European Search Report dated Mar. 6, 2019 in corresponding European Patent Application No. 18197038.5.

*Primary Examiner* — Kiho Kim

(74) *Attorney, Agent, or Firm* — Wenderoth, Lind & Ponack, L.L.P.

(57) ABSTRACT

Provided is a resin determination method including: placing an object on a placement surface with a diffusion reflectance of equal to or greater than 80% in an effective wavelength region of infrared light and with arithmetic mean roughness of equal to or greater than 0.25 μm and equal to or less than 25 μm; irradiating the object with infrared light; receiving reflected light from the object that has been irradiated with the infrared light; and determining a resin type based on a reflection spectrum or an absorption spectrum obtained by the reflected light.

11 Claims, 7 Drawing Sheets

(56) References Cited

U.S. PATENT DOCUMENTS

| | | | | |
|---|---|---|---|---|
| 2010/0140476 A1* | 6/2010 | Werner | ............... | G01J 3/02 |
| | | | | 250/339.07 |
| 2012/0305456 A1 | 12/2012 | Mase et al. | | |
| 2014/0203177 A1* | 7/2014 | Kinugawa | .......... | G01N 21/3563 |
| | | | | 250/339.11 |

FOREIGN PATENT DOCUMENTS

| | | |
|---|---|---|
| JP | 2014-157148 | 8/2014 |
| JP | 2015-121506 | 7/2015 |
| JP | 2017-101988 | 6/2017 |
| JP | 6160475 B | 7/2017 |
| WO | 2012/035785 | 3/2012 |

* cited by examiner

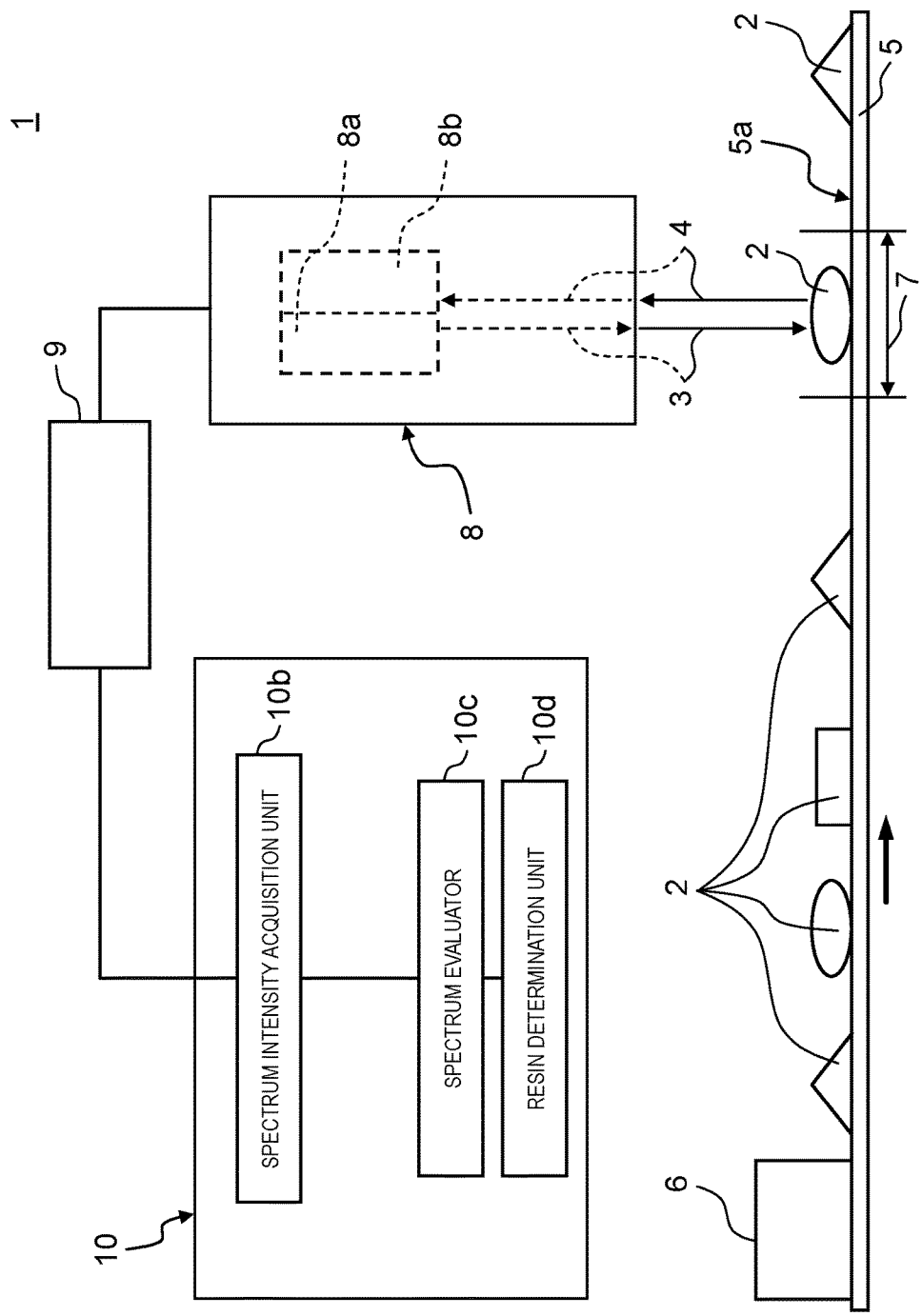

RESIN DETERMINATION METHOD AND RESIN DETERMINATION APPARATUS

BACKGROUND

1. Technical Field

The disclosure relates to a resin determination method and a resin determination apparatus for a resin type of an object that is a group of a plurality of types of small pieces.

2. Description of the Related Art

Environmental problems, such as global warming and exhaustion of resources, have occurred on a global scale due to mass consumption and mass disposal-type economic activities.

Under such circumstances, the Home Appliance Recycling Act has been enforced since April in 2001 in Japan for constructing a resource recycling-type society. The Home Appliance Recycling Act requires recycling of used home appliances (such as ACs, TVs, refrigerators, freezers, laundry washing machine, clothing driers). Therefore, the used home appliances are crushed into small pieces in home appliance recycling plants, are then sorted into each type of materials and are collected by using magnetic force, wind power, vibration, or the like, and are changed into resources again as recycle materials. Resin materials such as polypropylene (hereinafter, referred to as PP), polystyrene (hereinafter, referred to as PS), or acrylonitrile butadiene styrene (hereinafter, referred to as ABS) are used in many home appliances and are sorted into each resin type and are collected by sorting apparatuses utilizing light absorbing properties in a near-infrared region based on molecular structures of the resin.

An apparatus related to changing resin materials into resources again by utilizing the light absorbing properties in an infrared region has been proposed in Japanese Patent No. 6160475 (PTL 1). According to the technology disclosed in PTL 1, resin flake 20 is supplied from a hopper of flake supplier 22 to flake transporter 24 as illustrated in FIG. 5. Flake transporter 24 has a belt conveyor. Flake transporter 24 transports resin flake 20, which has been supplied from flake supplier 22, to discharge port 24a through a portion below reflectance measurer 21 by the belt conveyor. Sorted flake resin collector 28 is provided at a position to which resin flake 20 discharged from discharge port 24a falls. Two flake collection containers 28a and 28b are arranged in sorted flake resin collector 28.

Flake discriminator 26 is arranged between discharge port 24a of flake transporter 24 and sorted flake resin collector 28. Flake collection container 28a is arranged at a position to which resin flake 20 discharged from discharge port 24a naturally falls while flake collection container 28b is arranged at a position that is closer to discharge port 24a than to flake collection container 28a. Flake discriminator 26 causes resin flake 20 to fall into flake collection container 28b using air pressure by blowing air to resin flake 20 discharged from discharge port 24a, for example.

An output signal of resin identification unit 23 is input as a control signal to flake discriminator 26. In a case in which the output signal from resin identification unit 23 to flake discriminator 26 is a signal indicating that resin is ABS resin, for example, flake discriminator 26 blows the air to resin flake 20 discharged from discharge port 24a to cause resin flake 20 to fall into flake collection container 28b. Meanwhile, in a case in which the output signal from resin identification unit 23 to flake discriminator 26 is a signal indicating that resin is other than ABS resin, the air from flake discriminator 26 is not blown to resin flake 20 discharged from discharge port 24a.

Note that reflectance measurer 21 has, as optical systems, an irradiation optical system that irradiates resin flake 20 with infrared light and a light receiving optical system for reflected light that receives reflected light from resin flake 20 and guides the reflected light to a light detector. Further, reflectance measurer 21 has a received light optical system for incident light that switches optical paths as needed and guides infrared light after emission from the irradiation optical system before incidence on resin flake 20 to the light detector.

SUMMARY

According to the disclosure, there is provide a resin determination method including:

placing an object on a placement surface with a diffusion reflectance of equal to or greater than 80% in an effective wavelength region of infrared light and with arithmetic mean roughness Ra of equal to or greater than 0.25 μm and equal to or less than 25 μm;

irradiating the object with the infrared light;

receiving reflected light from the object that has been irradiated with the infrared light; and determining a resin type based on a reflection spectrum or an absorption spectrum obtained by the reflected light.

According to the disclosure, there is provided a resin determination apparatus including: a placement unit; an irradiator; a light receiver; and an arithmetic processor.

The placement unit has a placement surface on which an object is placed.

The irradiator irradiates the object with infrared light.

The light receiver receives reflected light from the object that has been irradiated with the infrared light.

The arithmetic processor determines a resin type of the object from a reflection spectrum or an absorption spectrum of the object based on the reflected light.

The placement surface has a diffusion reflectance of equal to or greater than 80% in an effective wavelength region of the infrared light and arithmetic mean roughness Ra of equal to or greater than 0.25 μm and equal to or less than 25 μm.

BRIEF DESCRIPTION OF THE DRAWINGS

FIG. 1 is a schematic diagram of a resin determination apparatus according to an embodiment;

DETAILED DESCRIPTION

Figure 2A:
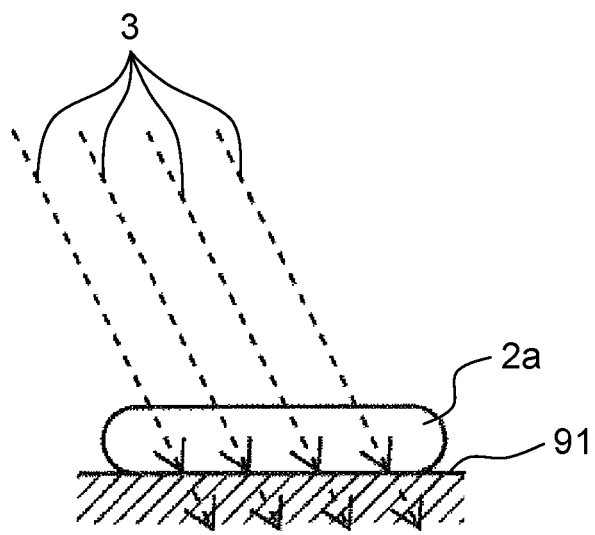
FIG. 2A is a schematic diagram of infrared reflection in a case in which transparent resin is placed on the resin determination apparatus in the related art.

According to the technology disclosed in Patent Literature 1, it is possible to determine a resin type since reflected light from resin colored with a white or black color, for example, can be detected. However, a resin type of transparent resin cannot be determined since the transparent resin transmits most parts of the infrared rays.

A resin type of transparent resin cannot be sorted with the infrared rays. Therefore, for resin pieces containing transparent resin, a visible light color hue sorting apparatus is used first to determine a color for whether or not the resin pieces are transparent. Then, a water specific gravity sorting apparatus is used to process resin, which has been determined to be transparent, with a flow of sorting resin floating in water, such as PP, and other types of resin, for example. Therefore, the determination of resin in the related art requires a plurality of apparatuses, and types of transparent resin that can be collected are limited.

Hereinafter, an embodiment of the disclosure will be described in detail with reference to drawings.

FIG. 1 is a schematic diagram of resin determination apparatus 1 according to the embodiment.

Resin determination apparatus 1 has, at least, infrared ray detector 8, arithmetic processor 10 as an example of the processor, and placement unit 5. Infrared ray detector 8 has irradiator 8a and light receiver 8b. Placement unit 5 has object placement surface 5a. Note that object placement surface 5a has a diffusion reflectance of equal to or greater than 80% in an effective wavelength region of infrared light (that is, infrared rays) emitted from irradiator 8a and has arithmetic mean roughness Ra of equal to or greater than 0.25 μm and equal to or less than 25 μm.

Resin 2 that is an object to be sorted is placed on object placement surface 5a. Irradiator 8a has a light source and irradiates resin 2, which is the object, with infrared light as an example of irradiation light 3 in detection region 7 in object placement surface 5a. Resin 2 is resin flake, for example.

Note that irradiation light 3 and reflected light 4 preferably include wavelength regions of equal to or greater than 1 μm and equal to or less than 3 μm as the effective wavelength region of the infrared light in order to utilize light absorbing properties of molecular structures of resin.

Resin 2 is irradiated with the infrared light as irradiation light 3 from irradiator 8a. Then, light receiver 8b receives reflected light 4 from resin 2 above (that is, immediately above or obliquely above) resin 2.

Arithmetic processor 10 determines a resin type of resin 2 from a reflection spectrum or an absorption spectrum of resin 2 based on reflected light 4.

Arithmetic processor 10 has, at least, spectrum intensity acquisition unit 10b, spectrum evaluator 10c, and resin determination unit 10d.

Spectrum intensity acquisition unit 10b acquires spectrum intensity based on reflected light 4. First, analog data of reflected light 4 received by light receiver 8b is input from light receiver 8b to spectrum intensity acquisition unit 10b in arithmetic processor 10 through digital data converter 9. Digital data converter 9 converts the analog data of reflected light 4 into digital data of reflected light 4. Spectrum intensity acquisition unit 10b calculates the reflection spectrum or the absorption spectrum of resin 2 based on the input digital data of reflected light 4. Then, the calculated reflection spectrum or the absorption spectrum is converted into a table or a graph representing a relationship between the reflection spectrum or the absorption spectrum and the spectrum intensity, for example, and spectrum intensity for determining resin is acquired from the table or the graph.

Spectrum evaluator 10c respectively obtains a plurality of correlation information pieces about the spectrum intensity acquired by spectrum intensity acquisition unit 10b and spectrum data of one or more resin types that is acquired in advance. Note that the correlation information is dimensionless quantities obtained by using a correlation coefficient, regression analysis, multivariate analysis, or the like.

Resin determination unit 10d determines, as a resin type of resin 2 that is the object, a resin type that is related to correlation information that is equal to or greater than a preset threshold value and is the highest from among a plurality of correlation information pieces obtained by spectrum evaluator 10c.

Infrared ray detector 8 has a function of irradiating resin 2 with infrared rays and a function of receiving reflected light 4 of irradiation light 3 reflected from resin 2. Infrared ray detector 8 is connected to arithmetic processor 10 via digital data converter 9.

Digital data converter 9 inputs an electric signal as analog data, which has been output in accordance with reflected light 4, from infrared ray detector 8. Then, digital data converter 9 converts the input electric signal into digital data and then outputs the digital data obtained through the conversion to arithmetic processor 10.

Arithmetic processor 10 calculates the reflection spectrum or the absorption spectrum of resin 2 based on the digital data output from digital data converter 9 and then acquires spectrum intensity by spectrum intensity acquisition unit 10b.

Note that in FIG. 1, placement unit 5 includes a belt conveyor in one example. The belt of the belt conveyor moves at a constant speed and can transport resin 2. Placement unit 5 transports resin 2 in a longitudinal direction of placement unit 5 from input region 6 to detection region 7. A placement surface of the belt conveyor for resin 2 is an object placement surface 5a that has a diffusion reflectance of equal to or greater than 80% in an effective wavelength region and has arithmetic mean roughness Ra of equal to or greater than 0.25 μm and equal to or less than 25 μm.

Here, infrared spectra of transparent resin obtained in the embodiment of the disclosure will be briefly described with reference to FIGS. 2A to 2D.

Figure 2B:
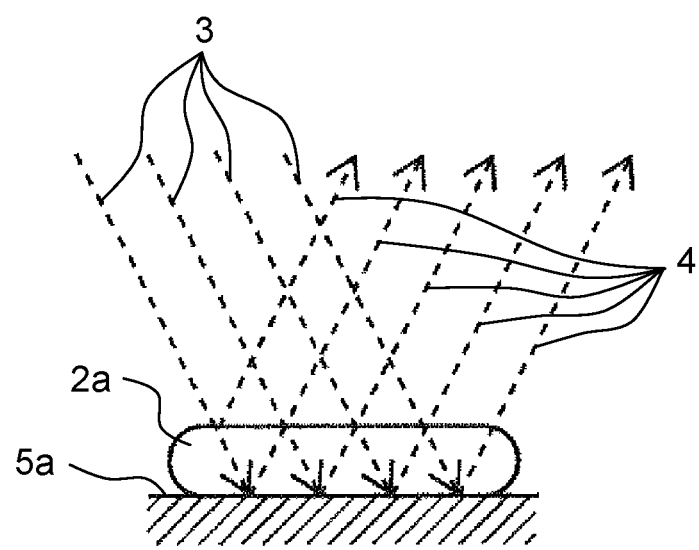
FIG. 2B is a schematic diagram of infrared reflection in a case in which transparent resin is placed on the resin determination apparatus according to the embodiment.
Figure 2C:
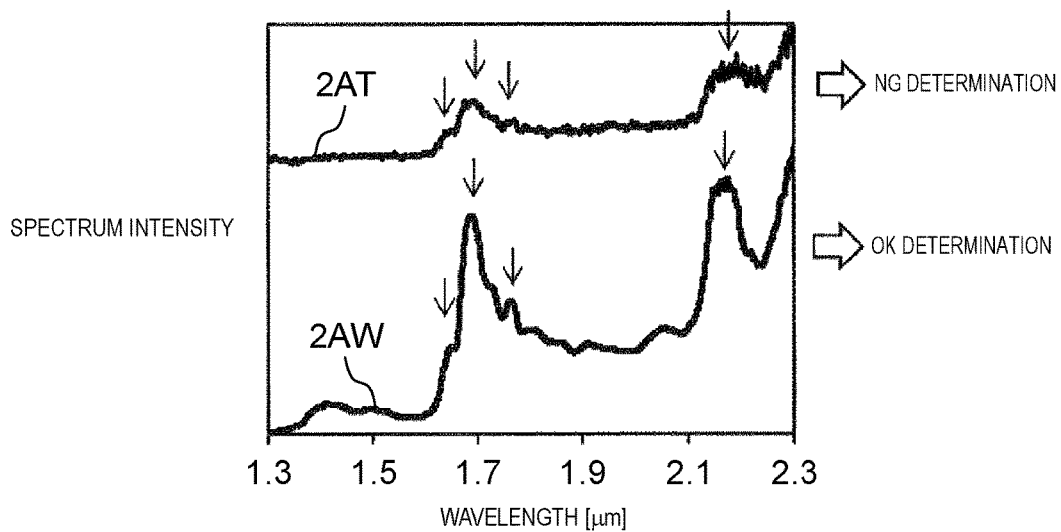
FIG. 2C is a diagram illustrating infrared spectra in a case in which the resin determination apparatus in the related art is used.
Figure 2D:
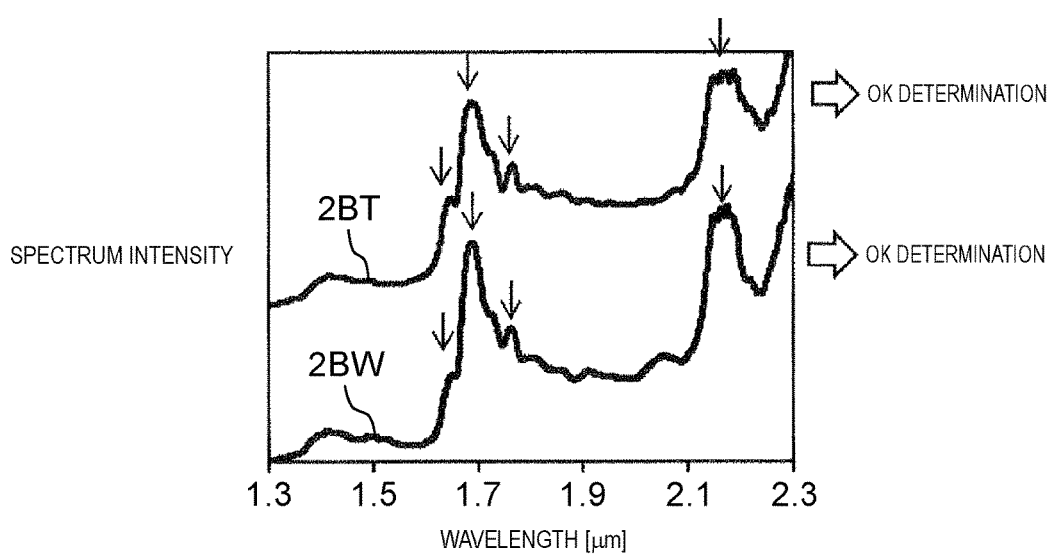
FIG. 2D is a diagram illustrating infrared spectra in a case in which the resin determination apparatus according to the embodiment is used.

FIG. 2A is a schematic diagram of reflection irradiation light 3 (infrared ray) in a case in which transparent resin 2a is placed on a placement surface of black belt 91 that has a diffusion reflectance of less than 80% in an effective wavelength region and is typically used in the related art. FIG. 2B is a schematic diagram of reflection of irradiation light 3 (infrared rays) in a case in which resin 2a (transparent resin) is placed on object placement surface 5a that has a diffusion reflectance of equal to or greater than 80% in an effective wavelength region of irradiation light 3 emitted from irradiator 8a and has arithmetic mean roughness Ra of equal to or greater than 0.25 μm and equal to or less than 25 μm according to the embodiment. In FIG. 2C, an infrared spectrum in a case in which white polystyrene resin (PS resin) is placed in FIG. 2A is represented as "2AW" while an infrared spectrum in a case in which transparent PS resin is placed is represented as "2AT". In FIG. 2D, an infrared spectrum in a case in which white PS resin is placed in FIG. 2B is represented as "2BW" while an infrared spectrum in a case in which transparent PS resin is placed is represented as "2BT".

In the configuration illustrated in FIG. 2A, irradiation light 3 is transmitted through transparent resin 2a while the infrared light that is irradiation light 3 is absorbed by black belt 91 that has a diffusion reflectance of less than 80% in the effective wavelength region. Therefore, the amount of reflected light from black belt 91 is significantly small. Therefore, as illustrated as "NG determination" in FIG. 2C, the amount of change in the infrared spectrum of the transparent PS resin is small, and it is difficult to determine a resin type. However, the amount of change in the infrared spectrum of the white PS resin is large, and it is possible to determine a resin type (see "2AW" in FIG. 2C).

Meanwhile, in the configuration illustrated in FIG. 2B, irradiation light 3 is transmitted through resin 2a, and resin 2a is placed on object placement surface 5a that has a diffusion reflectance of equal to or greater than 80% in an effective wavelength region and has arithmetic mean roughness Ra of equal to or greater than 0.25 μm and equal to or less than 25 μm. Therefore, the amount of reflected light 4 from resin 2a is large. Therefore, as illustrated as "OK determination" in FIG. 2D, a change in infrared spectrum that is close to that of the white PS resin (see "2BW" in FIG. 2D) can be obtained even in the case of the transparent PS resin (see "2BT" in FIG. 2D), and it is possible to determine a resin type.

Next, effects of object placement surface 5a with the arithmetic mean roughness Ra of equal to or greater than 0.25 μm and equal to or less than 25 μm will be described with reference to FIGS. 3A to 3C.

Figure 3A:
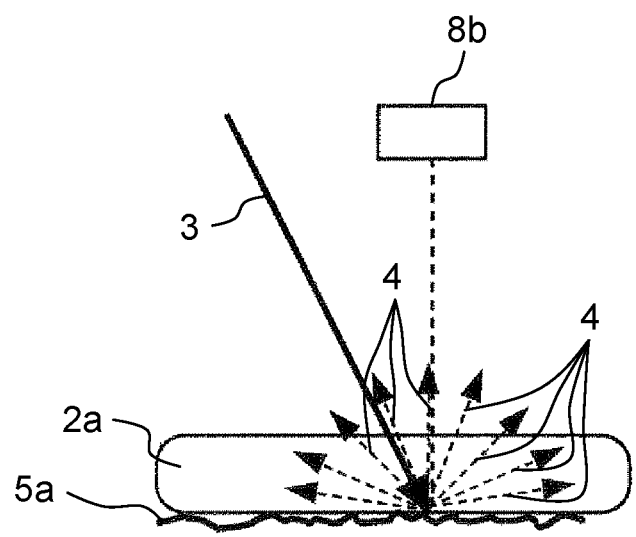
FIG. 3A is a schematic diagram of infrared reflection of the resin determination apparatus according to the embodiment.
Figure 3B:
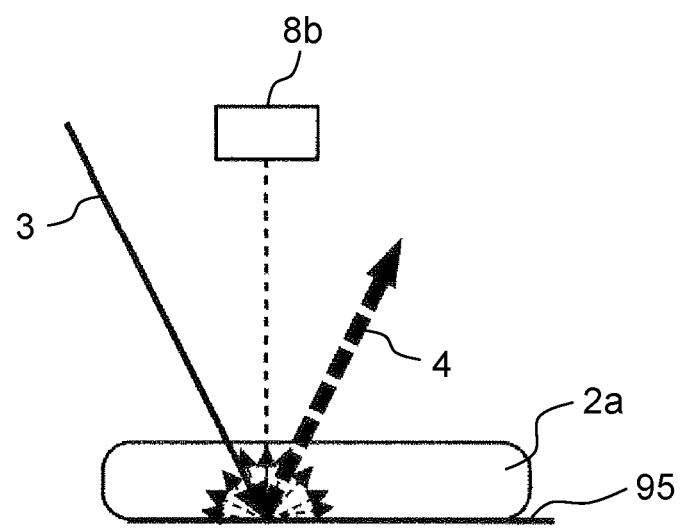
FIG. 3B is a schematic diagram of infrared reflection of the resin determination apparatus in the related art.
Figure 3C:
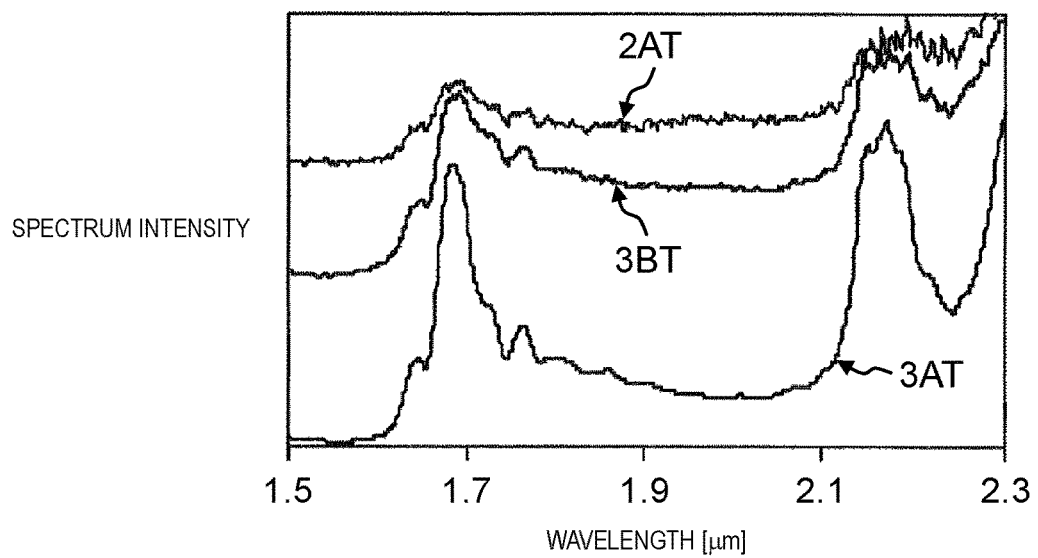
FIG. 3C is a diagram illustrating infrared spectra in a case in which the resin determination apparatuses according to the embodiment and in the related art are used.

FIG. 3A is a schematic diagram of reflection of irradiation light 3 (infrared rays) in a case in which resin 2a is placed on object placement surface 5a that has a diffusion reflectance of equal to or greater than 80% in an effective wavelength region and has arithmetic mean roughness Ra of equal to or greater than 0.25 μm and equal to or less than 25 μm according to the embodiment. FIG. 3B is a schematic diagram of reflection of irradiation light 3 (infrared rays) in a case in which resin 2a is placed on glossy surface 95 that has arithmetic mean roughness Ra of less than 0.25 μm. In FIG. 3C, an infrared spectrum in a case in which transparent PS resin 2a is placed on black belt 91 in FIG. 2A is represented as "2AT", an infrared spectrum in a case in which resin 2a is placed on object placement surface 5a in FIG. 3A is represented as "3AR", and an infrared spectrum in a case in which resin 2a is placed on glossy surface 95 in FIG. 3B is represented as "3BR".

As illustrated in FIG. 3A, irradiation light 3 is diffused and reflected by object placement surface 5a in a case in which resin 2a is placed on object placement surface 5a that has a diffusion reflectance of equal to or greater than 80% in an effective wavelength region and arithmetic mean roughness Ra of equal to or greater than 0.25 μm and equal to or less than 25 μm. Then, light receiver 8b can receive a large amount of reflected light 4 from resin 2a (see "3AR" in FIG. 3C). Meanwhile, as illustrated in FIG. 3B, the amount of direct reflection components of irradiation light 3 is large while the amount of diffused and reflected components from glossy surface 95 is small in reflected light 4 in the case in which placement surface (that is, the glossy surface) 95 that has the arithmetic mean roughness Ra of less than 0.25 μm is used. Therefore, light receiver 8b cannot receive a large amount of reflected light 4 (see "3BR" in FIG. 3C). Although not illustrated in the drawing, a spectrum measurement result that is similar to that from the placement surface with the arithmetic mean roughness Ra of less than 0.25 μm is obtained even from a placement surface with the arithmetic mean roughness Ra of greater than 25 μm since the amount of directly reflected components is larger than the amount of diffused and reflected components.

As such, the amount of change in the infrared spectrum is small, and it is difficult to determine a resin type in the case of transparent PS resin 2a in a case in which a placement surface with arithmetic mean roughness Ra of less than 0.25 μm and a placement surface with arithmetic mean roughness Ra of greater than 25 μm are used. However, it is possible to obtain a large amount of change in the infrared spectrum and to determine a resin type even in the case of transparent PS resin 2a using object placement surface 5a with a diffusion reflectance of equal to or greater than 80% in the effective wavelength region and with arithmetic mean roughness Ra of equal to or greater than 0.25 μm and equal to or less than 25 μm as in the embodiment.

Figure 4:
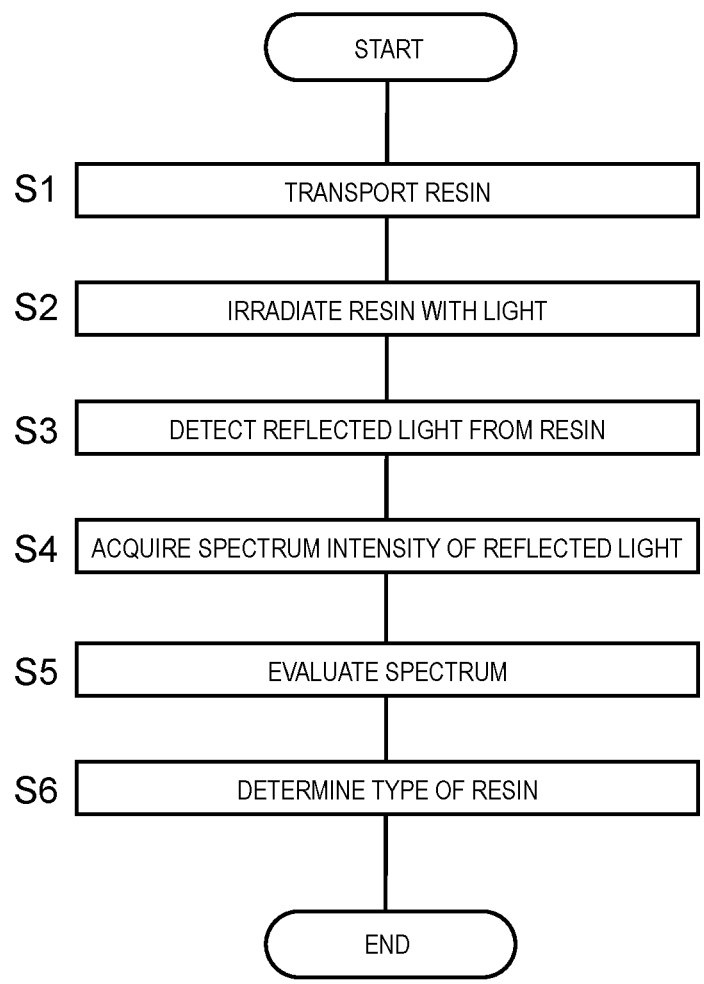
FIG. 4 is a flowchart illustrating a flow for determining a resin type by the resin determination apparatus according to the embodiment.
Figure 5:
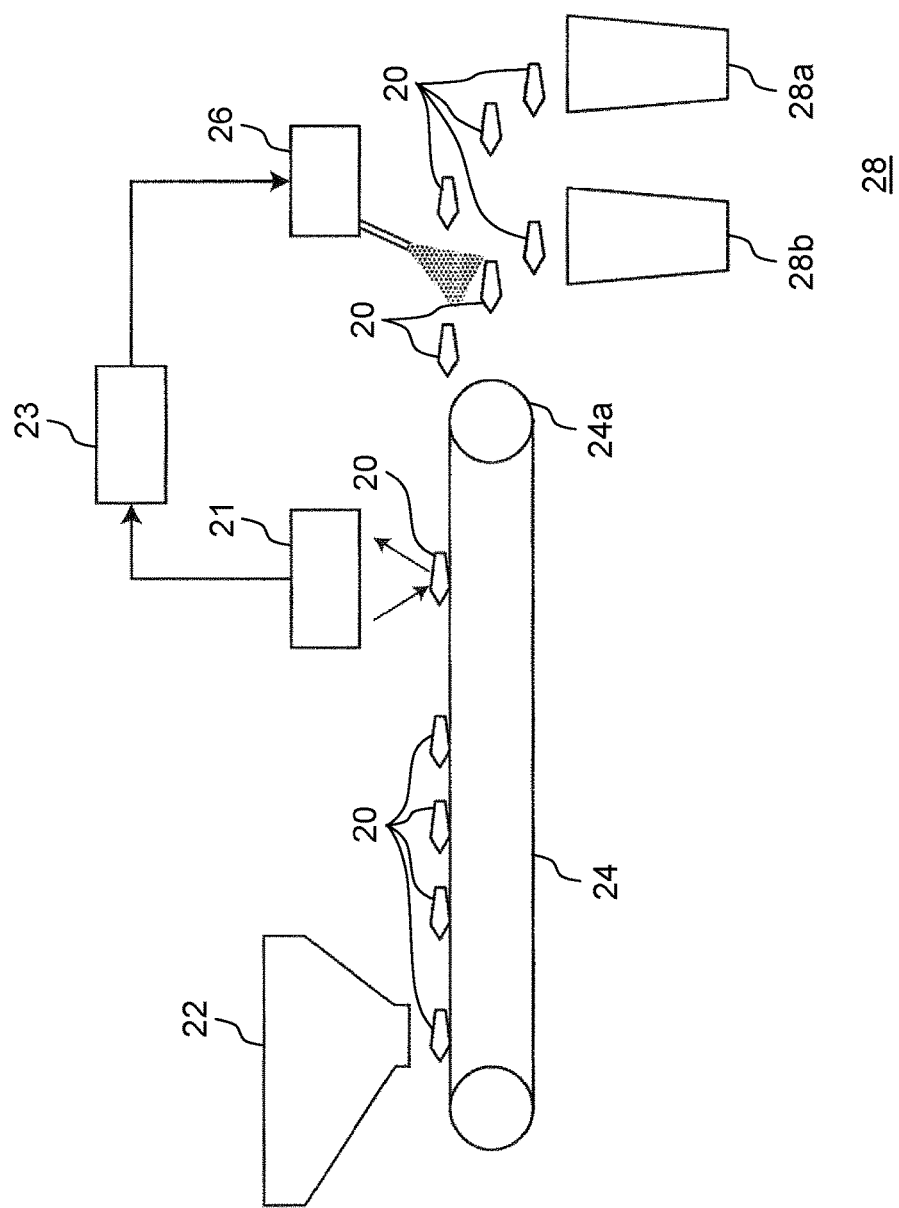
FIG. 5 is a schematic diagram of an apparatus used for resin determination in the related art as disclosed in Patent Literature 1.

Next, operations of resin determination apparatus 1 will be described with reference to the flowchart in FIG. 4.

First, in Step S1, resin 2 is input to input region 6 on placement unit 5 that moves at the constant speed, is placed on object placement surface 5a of placement unit 5, and is transported to detection region 7.

Then, in Step S2, infrared ray detector 8 irradiates resin 2 that has been placed on object placement surface 5a and has reached detection region 7 with irradiation light 3 from irradiator 8a. Here, resin 2 is in a state in which it is placed on object placement surface 5a with a diffusion reflectance of equal to or greater than 80% in the effective wavelength region and with arithmetic mean roughness Ra of equal to or greater than 0.25 μm and equal to or less than 25 μm when resin 2 is input from input region 6 above placement unit 5 to placement unit 5. Therefore, resin 2 placed on object placement surface 5a is irradiated with irradiation light 3 from irradiator 8a.

Then, in Step S3, infrared ray detector 8 detects reflected light 4 of irradiation light 3 from resin 2.

Then, in Step S4, analog data of reflected light 4 detected by infrared ray detector 8 is output from infrared ray detector 8 to arithmetic processor 10 through digital data converter 9. Digital data converter 9 converts the analog data of reflected light 4 into digital data of reflected light 4. Spectrum intensity acquisition unit 10b in arithmetic processor 10 calculates the reflection spectrum or the absorption spectrum of resin 2 based on the input digital data of reflected light 4 and generates the spectrum intensity for determining resin based on the reflection spectrum or the absorption spectrum.

Then, in Step S5, spectrum evaluator 10c calculates and evaluates a correlation coefficient between spectrum intensity for determining resin and a sample spectrum in one example of the correlation information, based on the spectrum intensity for determining resin that has been calculated by spectrum intensity acquisition unit 10b and the sample spectrum. Here, the sample spectrum means spectrum intensity of resin with known physical properties, which has been acquired in advance.

Then, in Step S6, a resin type is determined based on the correlation coefficient with the sample spectrum and a preset threshold value. Specifically, resin determination unit 10d determines that a resin type related to a correlation coefficient that is equal to or greater than the threshold value and is the largest is a resin type of resin 2 that is the object.

According to the resin determination method and the apparatus of the embodiment, resin 2 is placed on object placement surface 5a with a diffusion reflectance of equal to or greater than 80% in the effective wavelength region of irradiation light 3 (infrared light) and with arithmetic mean roughness Ra of equal to or greater than 0.25 µm and equal to or less than 25 µm as described above. With such a configuration, irradiation light 3 with which resin 2 is irradiated is diffused and reflected by resin 2, and light receiver 8b can receive a large amount of reflected light 4 from resin 2. Therefore, it is possible to determine a resin type of resin 2 at a high speed by using the infrared rays. Accordingly, object placement surface 5a can obtain a large amount of change in the infrared spectrum and can determine a resin type even in a case in which transparent resin (transparent PS resin 2a, for example) is used.

Note that appropriate combination of any embodiments or modification examples from among various embodiments or modification examples described above makes it possible to achieve effects that the combined embodiments or modification examples have.

According to the resin determination method and the resin determination apparatus of aspects of the disclosure, the object is placed on the object placement surface with a diffusion reflectance of equal to or greater than 80% in the effective wavelength region of the infrared light and with arithmetic mean roughness Ra of equal to or greater than 0.25 µm and equal to or less than 25 µm and is irradiated with the infrared light as described above. In this manner, the infrared light is diffused and reflected, and a large amount of reflected light can be received. As a result, it is possible to determine a resin type of the transparent resin by using the infrared rays.

It is possible to determine a resin type of transparent resin by using the resin determination method and the resin determination apparatus according to the aspects of the disclosure. Although transparent resin is sorted mainly by using a water specific gravity sorting apparatus capable of performing sorting regardless of resin colors in the related art, it is necessary to dry the resin and it is only possible to determine whether or not the resin floats in water. The resin determination method and the resin determination apparatus described above solve such problems, can determine a resin type of transparent resin by using infrared rays, and can thus further promote utilization of resin.

What is claimed is:

1. A resin determination method comprising:
placing an object on a placement surface with a diffusion reflectance of equal to or greater than 80% in an effective wavelength region of infrared light and with an arithmetic mean roughness of equal to or greater than 0.25 µm and equal to or less than 25 µm;
irradiating the object with the infrared light;
receiving diffused reflected light through the object from the placement surface, which has been irradiated with the infrared light, above the object; and
determining a resin type based on a reflection spectrum or an absorption spectrum obtained by the reflected light.

2. The resin determination method of claim 1, further comprising:
calculating a correlation coefficient between the reflection spectrum or the absorption spectrum obtained by the reflected light and a sample spectrum.

3. The resin determination method of claim 2, further comprising:
determining whether or not the correlation coefficient is equal to or greater than a preset threshold value.

4. The resin determination method of claim 1,
wherein an effective wavelength region of the infrared light is equal to or greater than 1 µm and equal to or less than 3 µm.

5. The resin determination method of claim 1, wherein in the irradiating step, an irradiating light irradiates the object, and a light receiver directly above the object receives the reflected light from the object.

6. A resin determination apparatus comprising:
a placement unit that has a placement surface on which an object is placed;
an irradiator that irradiates the object with infrared light;
a light receiver that receives diffused reflected light through the object from the placement surface, which has been irradiated with the infrared light, above the object; and
an arithmetic processor that determines a resin type of the object from a reflection spectrum or an absorption spectrum of the object based on the reflected light,
wherein the placement surface has a diffusion reflectance of equal to or greater than 80% in an effective wavelength region of the infrared light and an arithmetic mean roughness of equal to or greater than 0.25 µm and equal to or less than 25 µm.

7. The resin determination apparatus of claim 6,
wherein the arithmetic processor has a spectrum intensity acquisition unit that generates spectrum intensity from the reflected light from the light receiver.

8. The resin determination apparatus of claim 7,
wherein the arithmetic processor has a spectrum evaluator that calculates a correlation coefficient between the spectrum intensity generated by the spectrum intensity acquisition unit and a sample spectrum and evaluates the object.

9. The resin determination apparatus of claim 8,
wherein the arithmetic processor identifies a resin type of the object when the correlation coefficient is equal to or greater than a preset threshold value.

10. The resin determination apparatus of claim 6,
wherein an effective wavelength region of the infrared light is equal to or greater than 1 µm and equal to or less than 3 µm.

11. The resin determination apparatus of claim 6, wherein the light receiver receives reflected light from directly above the object.

* * * * *